United States Patent
Kolluri et al.

(10) Patent No.: US 7,462,152 B2
(45) Date of Patent: Dec. 9, 2008

(54) METHOD AND SYSTEM UTILIZING SPO₂ PLETHYSMOGRAPH SIGNAL TO REDUCE NIBP DETERMINATION TIME

(75) Inventors: Sai Kolluri, Tampa, FL (US); Lawrence T. Hersh, Tampa, FL (US); Richard Medero, Tampa, FL (US); Heather Menshouse, Odessa, FL (US)

(73) Assignee: The General Electric Company, Schenectady, NY (US)

( * ) Notice: Subject to any disclaimer, the term of this patent is extended or adjusted under 35 U.S.C. 154(b) by 122 days.

(21) Appl. No.: 11/470,698

(22) Filed: Sep. 7, 2006

(65) Prior Publication Data

US 2008/0082006 A1 Apr. 3, 2008

(51) Int. Cl.
*A61B 5/02* (2006.01)

(52) U.S. Cl. ............ 600/490; 600/495; 600/500; 600/494; 600/493

(58) Field of Classification Search .......... 600/481, 600/483, 485, 490–503
See application file for complete search history.

(56) References Cited

U.S. PATENT DOCUMENTS

| | | | |
|---|---|---|---|
| 4,360,029 A | 11/1982 | Ramsey, III | |
| 4,394,034 A | 7/1983 | Murphy et al. | |
| 4,461,226 A | 7/1984 | Tajima | |
| 4,543,962 A | 10/1985 | Medero et al. | |
| 4,546,775 A | 10/1985 | Medero | |
| 4,638,810 A | 1/1987 | Ramsey, III et al. | |
| 4,754,761 A | 7/1988 | Ramsey, III et al. | |
| 4,796,184 A | 1/1989 | Bahr et al. | |
| 4,889,133 A | 12/1989 | Nelson et al. | |
| 4,949,710 A | 8/1990 | Dorsett et al. | |
| 5,170,795 A | 12/1992 | Ramsey, III et al. | |
| 5,337,751 A * | 8/1994 | Newell et al. | 600/495 |
| 5,577,508 A | 11/1996 | Medero | |
| 5,579,776 A | 12/1996 | Medero | |
| 5,590,662 A | 1/1997 | Hersh et al. | |
| 5,704,362 A | 1/1998 | Hersh et al. | |
| 6,027,453 A * | 2/2000 | Miwa et al. | 600/485 |
| 6,027,455 A * | 2/2000 | Inukai et al. | 600/490 |
| 6,036,651 A * | 3/2000 | Inukai et al. | 600/485 |
| 6,036,652 A * | 3/2000 | Inukai et al. | 600/493 |
| 6,358,213 B1 | 3/2002 | Friedman et al. | |
| 6,423,010 B1 | 7/2002 | Friedman et al. | |
| 6,428,481 B1 * | 8/2002 | Inukai et al. | 600/485 |
| 6,440,080 B1 | 8/2002 | Booth et al. | |
| 6,491,638 B2 * | 12/2002 | Oka | 600/494 |
| 6,582,374 B2 * | 6/2003 | Yokozeki | 600/494 |

(Continued)

*Primary Examiner*—Charles A Marmor, II
*Assistant Examiner*—Navin Natnithithadha
(74) *Attorney, Agent, or Firm*—Andrus, Sceales, Starke & Sawall, LLP

(57) ABSTRACT

A method and system for operating a non-invasive blood pressure monitor that utilizes an SpO₂ plethysmographic signal to reduce the time required to obtain an estimation of a patient's blood pressure. During operation of the NIBP monitor, the NIBP monitor utilizes the SpO₂ plethysmographic signal to determine a timing period and a deflation period for each pulse associated with the patient's heartbeat. Upon receiving an oscillation pulse, the NIBP monitor determines the oscillation amplitude during the timing period and deflates the blood pressure cuff during the deflation period immediately following the timing period. Preferably, the deflation period occurs during the same oscillation pulse used to calculate the oscillation pulse amplitude to decrease the amount of time required to obtain a blood pressure estimate from the patient.

18 Claims, 6 Drawing Sheets

U.S. PATENT DOCUMENTS 6,808,496 B2 * 10/2004 Oka et al. .................. 600/485
2002/0082507 A1    6/2002 Kolluri et al.
2002/0161305 A1 * 10/2002 Oka ........................... 600/490
2003/0097074 A1 * 5/2003 Oka et al. ................... 600/490
2007/0049834 A1 * 3/2007 Tao et al. .................... 600/494

* cited by examiner

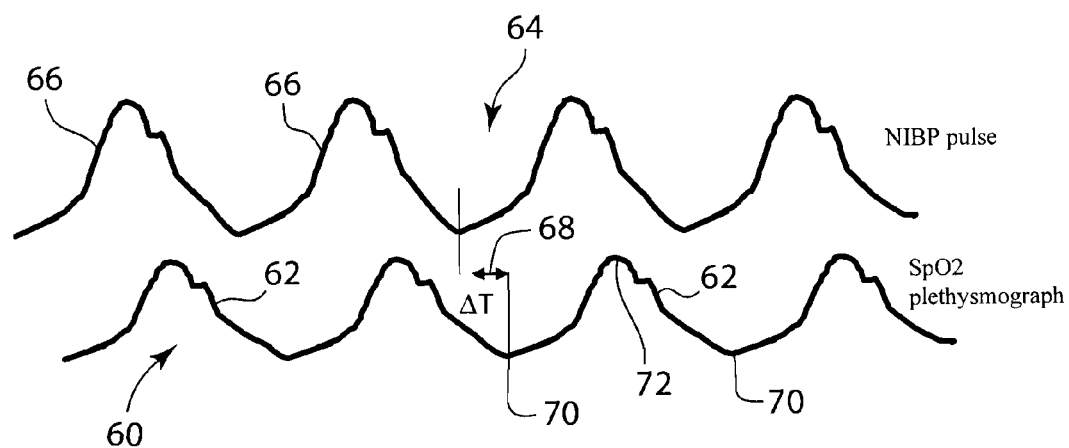
FIG. 3
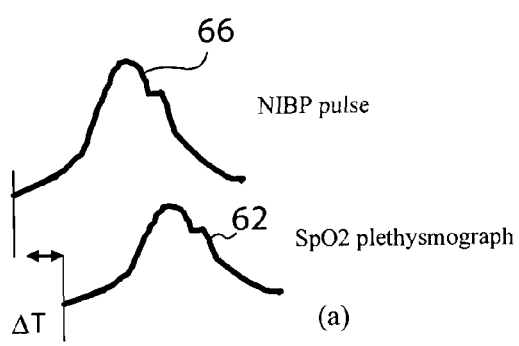
(a)
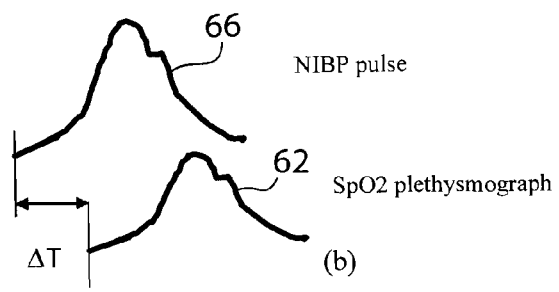
(b)
FIG. 5

METHOD AND SYSTEM UTILIZING SPO₂ PLETHYSMOGRAPH SIGNAL TO REDUCE NIBP DETERMINATION TIME

FIELD OF THE INVENTION

The present invention generally relates to a method of operating an automatic blood pressure measuring apparatus. More specifically, the present invention relates to a method of utilizing an $SpO_2$ plethysmograph waveform to optimize the operation of an automated, non-invasive blood pressure (NIBP) monitor to reduce the period of time required to determine a patient's blood pressure.

BACKGROUND OF THE INVENTION

Automated blood pressure monitoring has rapidly become an accepted and, in many cases, essential aspect of human healthcare. Such monitors are now a conventional part of the patient environment in emergency rooms, intensive and critical care units, and in the operating theater.

The oscillometric method of measuring blood pressure involves applying an inflatable cuff around an extremity of a patient's body, such as a patient's upper arm. The cuff is inflated to a pressure above the patient's systolic pressure and then the cuff pressure is reduced either continuously or incrementally in a series of small pressure steps. A pressure transducer measures the cuff pressure, including the pressure fluctuations resulting from the heart pumping activity that causes pressure and volume changes in the artery under the cuff. The data from the pressure transducer is used to compute the patient's systolic pressure, mean arterial pressure (MAP) and diastolic pressure.

An example of the oscillometric method of measuring blood pressure is shown and described in U.S. Pat. Nos. 4,360,029; 4,394,034; and 4,638,810, which are commonly assigned with the present invention.

During the use of a conventional NIBP monitoring system, the blood pressure cuff is placed around the arm of a patient and is inflated to an initial inflation pressure that fully occludes the brachial artery to prevent blood flow. The cuff is then progressively deflated from the initial inflation pressure and the pressure transducer detects pressure pulses associated with the patient's heartbeat as blood begins to flow past the pressure cuff. Typical blood pressure algorithms utilized within the NIBP monitor deflate the pressure cuff in a series of pressure steps determined by the algorithm used to operate the NIBP monitor. As an example, the pressure cuff is typically decreased in equal pressure steps of a fixed amount (e.g. 8 mmHg or similar value). The deflation of the blood pressure cuff occurs after an NIBP oscillation pulse amplitude has been recorded for the current pressure step. In this method, the cuff pressure deflation is not synchronized with the arrival of the next blood pressure pulse. Thus, the prior art algorithms do not optimize the timing of the cuff deflation.

During the deflation of the cuff pressure, the peak amplitude of the oscillation pulses detected by the system will normally increase from a lower level to a relative maximum, and thereafter decrease. These amplitudes form an oscillometric envelope for the patient. The cuff pressure at which the oscillation pulses have a maximum value has been found to be representative of the mean arterial pressure (MAP) of the patient. Systolic and diastolic pressures are then derived either as a predetermined fraction of the oscillation size at MAP, or by more sophisticated methods of direct processing of the oscillation complexes.

The step deflation technique as set forth in the Ramsey patents is the commercial standard of operation. A large percentage of clinically acceptable automated blood pressure monitors utilize the step deflation rationale. When in use, the blood pressure cuff is placed on a patient and the operator usually sets a time interval, typically from one to ninety minutes, at which blood pressure measurements are to be made. The non-invasive blood pressure (NIBP) monitor automatically starts a blood pressure determination at the end of the set time interval.

Generally, conventional NIBP monitors of the type described in the above-mentioned patents use oscillation pulse amplitude matching at each pressure step as one of the ways to discriminate good oscillations from artifacts and noise. In particular, pairs of oscillation pulses are compared at each pressure step to determine if the pulses are similar in amplitude and similar in other attributes, such as shape, area under the oscillation curve, slope, and the like. If the oscillation pulses compare within predetermined limits, the average pulse amplitude for the two pulses and the cuff pressure are stored and the pressure cuff is deflated to the next pressure level. However, if the oscillation pulses do not compare favorably, the attributes of the earlier oscillation pulse are typically ignored and the attributes of the later oscillation pulse are stored. The monitor does not deflate the blood pressure cuff and instead waits for another oscillation pulse to compare with the oscillation pulse stored. This process continues until two successive oscillation pulses are matched or a time limit is exceeded.

Although the step deflation technique described above can eliminate or reduce the effect artifacts have in the blood pressure determination, the step deflation technique typically requires the detection of two oscillation pulses during each pressure step. Even when detected oscillation pulses are very clean and artifact-free, the step deflation technique has an inherent delay in order to control the pressure level of each step. Therefore, the amount of time required to make the blood pressure determination will be extended by the time that the technique uses at each pressure step to control the pressure. It is desirable to provide a system and method to reduce the amount of time required to estimate a patient's blood pressure to enhance the performance of an NIBP system.

SUMMARY OF THE INVENTION

The following describes a method and system for monitoring the blood pressure in a patient that utilizes an $SpO_2$ plethysmographic waveform to improve the performance of a non-invasive blood pressure (NIBP) monitor. The combined blood pressure monitoring system includes a NIBP monitor having a blood pressure cuff that is placed upon the patient. The blood pressure cuff is selectively inflated and deflated by a central processor, which controls the availability of pressurized air to the cuff and the position of valves that release air from the cuff. During the deflation of the blood pressure cuff, oscillation pulses are detected and the central processor calculates a pulse amplitude for each pulse, which are utilized to calculate the blood pressure of a patient.

The combined system further includes a sensing system that delivers a plethysmographic waveform to the central processor. Preferably, the sensing system is a pulse oximeter monitor including a finger probe sensor positioned on the finger of the patient. However, other locations (feet/forehead/ear) are contemplated and other sensing technologies such as reflectance, impedance or a piezo element in a cuff can also be used. The pulse oximeter monitor delivers a plethysmographic waveform including a series of SpO$_2$ values to the central processor of the NIBP monitoring system. Since the plethysmographic waveform and the oscillation pulses detected by the pressure transducer of the NIBP monitor correspond directly to the patient's heartbeat, the duration of the pulses within each of the two signals are the same. Thus, timing calculations determined from either the series of NIBP pulses or the plethysmographic waveform can be utilized when analyzing the oscillation pulses within the NIBP waveform.

Based upon either the NIBP or the plethysmographic waveform, the central processor of the NIBP monitor calculates a timing period and a deflation period associated with each of the patient's heartbeats. Preferably, the timing period extends from the diastolic point on the oscillation pulse to just past the systolic peak of the oscillation pulse. Following the timing period, the deflation period extends from just past the systolic peak to the diastolic point of the next oscillation pulse.

The central processor of the NIBP monitoring system detects the beginning of an oscillation pulse within the NIBP waveform. Upon detection of the beginning of an oscillation pulse, the NIBP monitor obtains amplitude information from the pulse during the timing period, which extends just past the systolic peak of the oscillation pulse. Since the oscillation pulse amplitude is determined from the diastolic point to the systolic peak, the portion of the oscillation pulse following the systolic peak is not required for the calculation of the oscillation amplitude. Thus, once the timing period expires, the central processor begins to deflate the pressure cuff for the deflation period. The deflation of the pressure cuff during the deflation period of the oscillation pulse reduces the amount of time required to perform a blood pressure calculation on a patient utilizing the NIBP monitoring system.

During the deflation period, the pressure level of the blood pressure cuff is decreased by a pressure step from a first pressure level to a second pressure level. The pressure value of the pressure step is determined by the amount of time the deflate valve is allowed to remain open, which in turn is dictated by the deflation period. Thus, unlike other prior algorithms used for operating an NIBP monitor, the algorithm of the present invention deflates the pressure cuff for a set period of time rather than a defined pressure step.

At each pressure level, a single oscillation amplitude is determined by the NIBP monitoring system. Following the determination of the oscillation amplitude, the central processor of the NIBP monitoring system determines whether a corresponding plethysmographic pulse is received within a time differential ΔT from the oscillation pulse. If a plethysmographic pulse is received within the time differential, the system recognizes the oscillation pulse as valid and not an artifact. However, if a plethysmographic pulse is not received within the time differential, the processor of the NIBP monitoring system assigns a weighting factor to the pulse amplitude, which causes the pulse amplitude to be effectively eliminated from the calculation of the patient's blood pressure. Alternatively, the weighting factor assigned to each pulse amplitude can be dependent upon various oscillation and/or plethysmographic pulse parameters, such as the size, height and shape of the pulse compared to other pulses detected from the NIBP waveform.

By utilizing the system and method described, the NIBP monitoring system can reduce the amount of time required to obtain a blood pressure estimate from a patient while not sacrificing the accuracy of the measurement. Specifically, by utilizing a portion of each oscillation pulse to deflate the pressure cuff while obtaining only a single amplitude measurement from each oscillation pulse, the NIBP monitoring system can significantly reduce the amount of time required to obtain a blood pressure estimate.

BRIEF DESCRIPTION OF THE DRAWINGS

The drawings illustrate the best mode presently contemplated of carrying out the invention. In the drawings:

FIG. 3 illustrates a graphical comparison of an NIBP waveform and a SpO$_2$ plethysmographic waveform;

FIGS. 5A and 5B illustrate the time differential between an NIBP oscillation and a plethysmographic pulse for the same patient heartbeat;

DETAILED DESCRIPTION OF THE INVENTION

Figure 1:
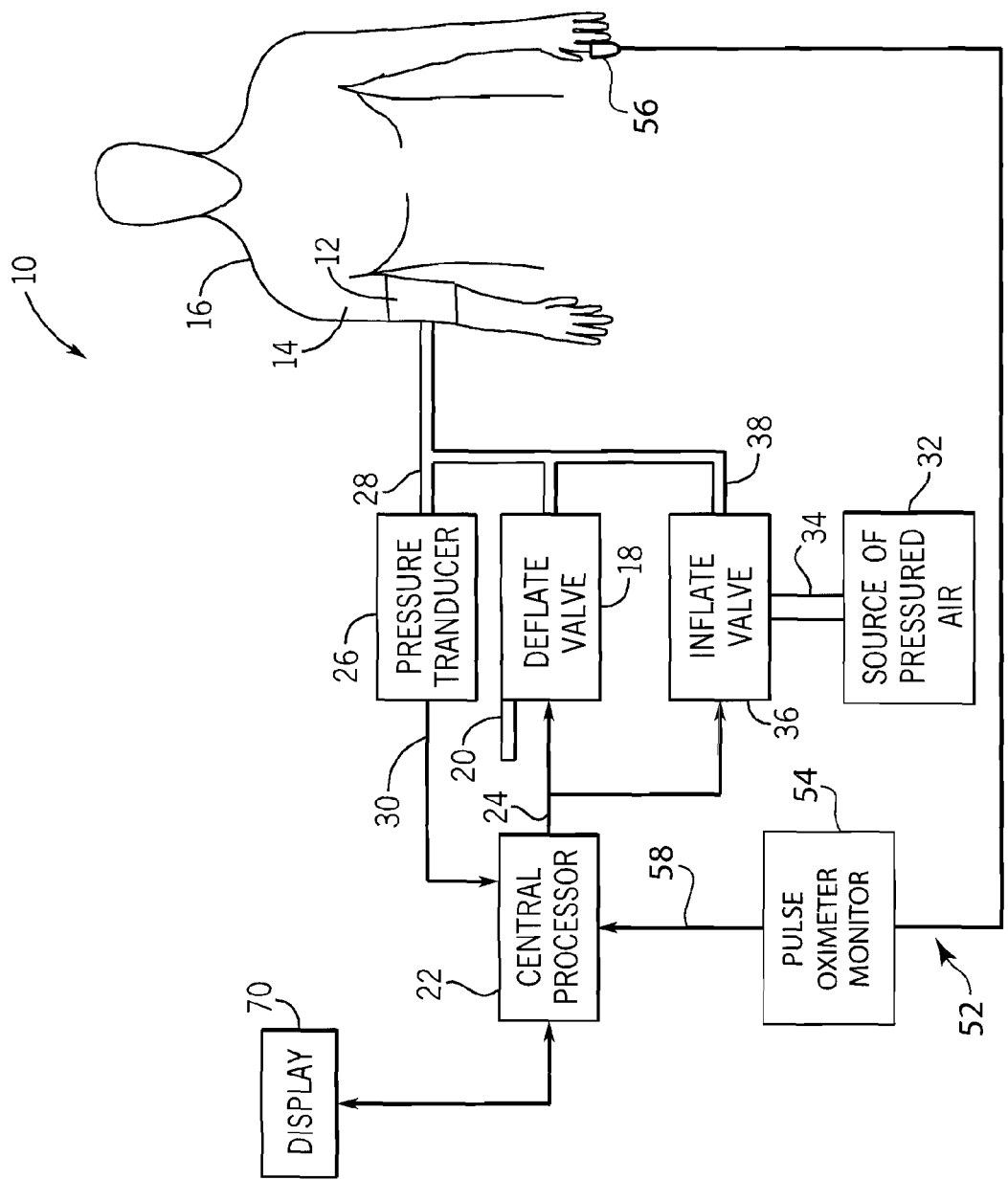
FIG. 1 is a block diagram of a system for monitoring blood pressure in a patient using an NIBP monitor and a pulse oximeter monitoring system.

FIG. 1 generally illustrates a non-invasive blood pressure (NIBP) monitoring system 10 of conventional construction. The NIBP monitoring system 10 includes a blood pressure cuff 12 placed on the arm 14 of a patient 16. The blood pressure cuff 12 can be inflated and deflated for occluding the brachial artery of the patient 16 when in the fully inflated condition. As the blood pressure cuff 12 is deflated using the deflate valve 18 having exhaust 20, the arterial occlusion is gradually relieved. The deflation of the blood pressure cuff 12 by the deflate valve 18 is controlled by a central processor 22 through the control line 24.

A pressure transducer 26 is coupled by duct 28 to the blood pressure cuff 12 for sensing the pressure within the cuff 12. In accordance with conventional oscillometric techniques, the pressure transducer 26 is used to sense pressure oscillations in the cuff 12 that are generated by pressure changes in the artery under the cuff. The electrical oscillation signals from the pressure transducer 26 are obtained by the central processor 22, using an analog-to digital converter, through connection line 30.

A source of pressurized air 32, such as an air compressor or compressed gas cylinder, is connected by duct 34. In an embodiment incorporating an air compressor, the air compressor is coupled directly to the duct 38. However, if the source of pressurized air is supplied by a compressed gas cylinder, an inflate valve 36 is positioned between the source 32 and the duct 38. The operation of the inflate valve 36 is controlled by the central processor 22 through the control line 24. Thus, the inflation and deflation of the blood pressure cuff 12 is controlled by the central processor 22 through the deflate valve 18 and the inflate valve 36, respectively.

From the standpoint of the principles of the present invention, the processing of the oscillation signals from first pressure transducer 26 by the central processor 22 to produce blood pressure data, and optionally to reject artifact data, can be conducted in accordance with the prior art teachings of the above-referenced Ramsey '029 and '034 patents. Alternatively, the blood pressure can be determined in accordance with the teachings of Medero et al in U.S. Pat. No. 4,543,962, of Medero in U.S. Pat. No. 4,546,775, of Hood, Jr. et al in U.S. Pat. No. 4,461,266, of Ramsey, III et al in U.S. Pat. No. 4,638,810, of Ramsey III et al in U.S. Pat. No. 4,754,761, of Ramsey III et al in U.S. Pat. No. 5,170,795, of Ramsey III et al in U.S. Pat. No. 5,052,397, of Medero in U.S. Pat. No. 5,577,508 and of Hersh et al in U.S. Pat. No. 5,590,662, all of which are commonly assigned herewith and the disclosures of which are hereby incorporated by reference. In any event, it is desirable to use any of the known techniques to determine the quality of the oscillation complexes received at each cuff pressure so that the blood pressure determination is made using the physiological relevant cuff pressure oscillations resulting from a heartbeat rather than from artifacts.

Figure 2:
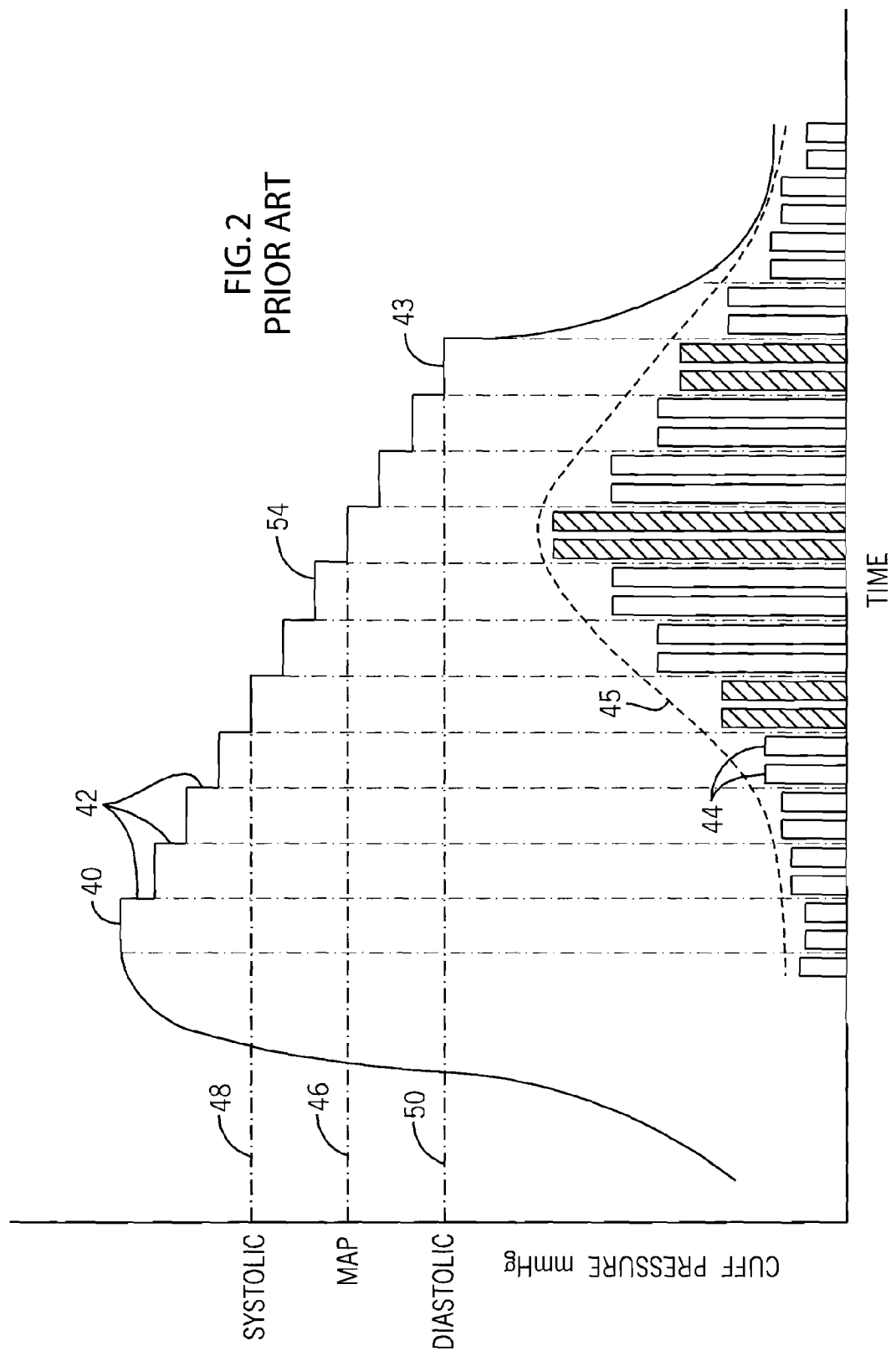
FIG. 2 is a graph depicting a prior art method of operating an NIBP monitor by obtaining at least two oscillation pulse amplitudes at each of a series of pressure steps.

During normal operation of the NIBP monitoring system 10 shown in FIG. 1, the blood pressure cuff 12 is initially placed on the patient 16, typically around the subject's upper arm 14 over the brachial artery. At the inception of the measuring cycle, the blood pressure cuff 12 is inflated to a pressure that fully occludes the brachial artery, i.e., prevents blood from flowing through the brachial artery at any point in the heart cycle. In FIG. 2, the initial inflation pressure is illustrated by reference number 40.

After the blood pressure cuff has been inflated to the initial inflation pressure 40, the deflate valve is actuated by the central processor to deflate the cuff in a series of pressure steps 42. Although various values for each pressure step 42 can be utilized, in an exemplary example, each pressure step 42 is typically about 8 mmHg.

After each pressure step 42, the NIBP monitoring system detects and records the amplitude 44 of two oscillation pulses for the current cuff pressure level. The pressure transducer measures the internal cuff pressure and provides an analog signal characterizing the blood pressure oscillatory complexes. The peak values of the complex signals are determined within the central processor.

As the cuff pressure decreases from the initial inflation pressure, the NIBP monitoring system detects pressure oscillations 44 and records the pressure oscillations for the current cuff pressure. The central processor within the NIBP monitoring system can then calculate the MAP 46, systolic pressure 48 and diastolic pressure 50.

As the measurement cycles progress, the peak amplitude of the oscillation pulses generally become monotonically larger to a maximum and then become monotonically smaller as the cuff pressure continues toward full deflation, as illustrated by the bell-shaped graph 45 in FIG. 2. The peak amplitude of the cuff pressure oscillation complexes, and the corresponding occluding-cuff pressure values, are retained in the central processor memory. The oscillometric measurements are used by the central processor to calculate the mean arterial pressure (MAP) 46, the systolic pressure 48 and the diastolic pressure 50 in a known manner.

Referring back to FIG. 1, the system of the present invention further includes a sensing system 52 for obtaining a plethysmographic waveform from the patient 16. In the embodiment of the invention illustrated in FIG. 1, the sensing system 52 is a pulse oximeter monitoring system 54 having a finger probe 56 positioned on the patient 16 to determine the $SpO_2$ values on the patient 16.

The pulse oximeter monitoring system 54 generates an $SpO_2$ plethysmograph signal that is provided to the central processor 22 of the NIBP monitoring system 10 through a communication line 58. In addition to providing the $SpO_2$ values for the patient, the pulse oximeter monitor 54 obtains a plethysmographic waveform 60 (FIG. 3) that includes a series of time-spaced pulses 62 that each result from a beat of the patient's heart. Since the finger probe 56 is attached to the patient 16, the pulse oximeter monitoring system 54 continuously monitors the patient and generates a continuous plethysmographic waveform 60 having the series of time-spaced pulses 62.

As indicated in FIG. 3, when the NIBP monitoring system is activated to obtain the blood pressure from the patient, the NIBP monitoring system obtains an NIBP waveform 64 that also includes a series of oscillation pulses 66 each corresponding to the patient's heartbeat. Since both the plethysmographic waveform 60 and the NIBP waveform 64 include a series of spaced pulses corresponding to the patient's heartbeat, the duration of each of the plethysmographic pulses 62 generally corresponds to the duration of the oscillation pulses 66. However, since the blood pressure cuff of the NIBP monitoring system is typically located closer to the patient's heart than the finger probe of the pulse oximeter monitoring system, the oscillation pulses 66 generally leads the corresponding plethysmographic pulses 62 by a time differential $\Delta T$, referred to by arrow 68. If the NIBP waveform 64 is obtained with very little noise or artifacts, each of the oscillation pulses 66 will generally lead the corresponding plethysmographic pulse 62 by the same time differential $\Delta T$. While $\Delta T$ remains constant at a pressure step, the $\Delta T$ changes with cuff pressure and proper allowances are made to gate the pulses.

As described previously, the pulse oximeter monitoring system 54 shown in FIG. 1 communicates the plethysmographic waveform including the series of time-spaced pulses to the central processor 22. Upon receiving the plethysmographic waveform 60, the central processor 22 can perform various timing calculations on each of the pulses contained within the waveform. As an example, the central processor can calculate a timing period from the diastolic point 70 to the systolic peak 72 for each of the individual plethysmographic pulses 62, as best shown in FIG. 3. Following the systolic peak 72, the central processor can determine the amount of time from the systolic peak 72 to the diastolic point 70 for the next pulse 62. Since the central processor is receiving a continuous series of plethysmographic pulses 62, the central processor can calculate an average for the rise from the diastolic point 70 to the systolic peak 72 and subsequent decline from the systolic peak 72 to the next diastolic point 70. Since the plethysmographic pulses 62 correspond in duration to the oscillation pulses 66 from the NIBP waveform 64, the calculated time periods from the plethysmographic pulses can be utilized by the NIBP monitoring system 10 to optimize the operation of the NIBP monitoring system.

Although the timing period from the diastolic point 70 to the systolic peak 72 is shown in FIG. 3 as being calculated from the plethysmographic waveform 60, it should be understood that the same timing period could also be calculated by using the NIBP waveform 64 since each of the oscillation pulses 66 has the same duration as the plethysmographic pulses 62. Thus, the timing period, as well as other time-based periods within each of the pulses, can be calculated from either the plethysmographic waveform 60 or the NIBP waveform 64. Additionally, the pulse-based timing period could also be calculated from other signals, such as an ECG.

Figure 4:
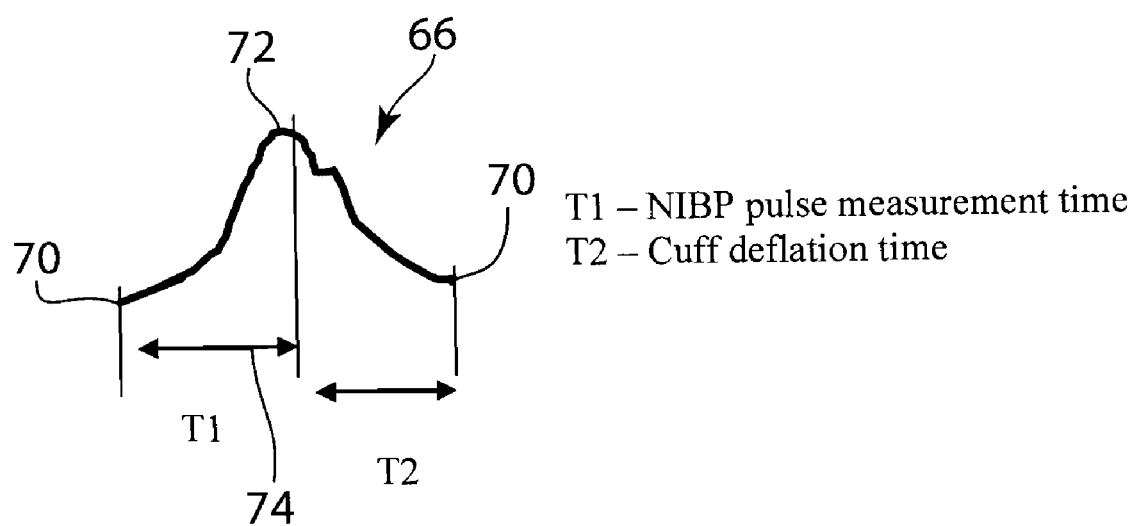
FIG. 4 is a detailed view of a single NIBP pulse.

Referring now to FIG. 4, thereshown is a typical NIBP oscillation pulse 66 isolated from the NIBP waveform. As shown in FIG. 4, the central processor can calculate a timing period T1 represented by arrow 74. The timing period T1 begins at the diastolic point 70 and extends slightly past the systolic peak 72 of the oscillation pulse 66. Following the timing period T1, the central processor also calculates a deflation period T2 that begins immediately following the timing period T1 and extends to the diastolic point 70 for the next oscillation pulse 66. For a typical patient, assuming the pulse rate is sixty beats per minute, the timing period T1 will represent about one-third of the pulse period while the deflate period will represent approximately two-thirds of the pulse period. Thus, as an illustrated example, the timing period T1 will be slightly larger than 0.33 seconds while the deflate period, T2, will be slightly less than 0.67 seconds. These values, of course, will vary for each individual patient.

As described previously, the NIBP monitoring system obtains an oscillation pulse amplitude for each of the oscillation pulses detected during the measurement of the patient's blood pressure. The pulse amplitude is measured as the height of the pulse from the previous diastolic point to the peak of the oscillation (systolic peak 72). Thus, as clearly illustrated in FIG. 4, the NIBP monitoring system can determine the pulse amplitude by analyzing the signal from the pressure transducer during the timing period T1, which extends just past the systolic peak 72. Following the systolic peak 72, the remaining portion of each oscillation pulse 66 is irrelevant in determining the oscillation pulse amplitude. In accordance with the present invention, the remaining portion of the oscillation pulse 66 will be utilized to deflate the pressure cuff during the deflation period T2.

Figure 6:
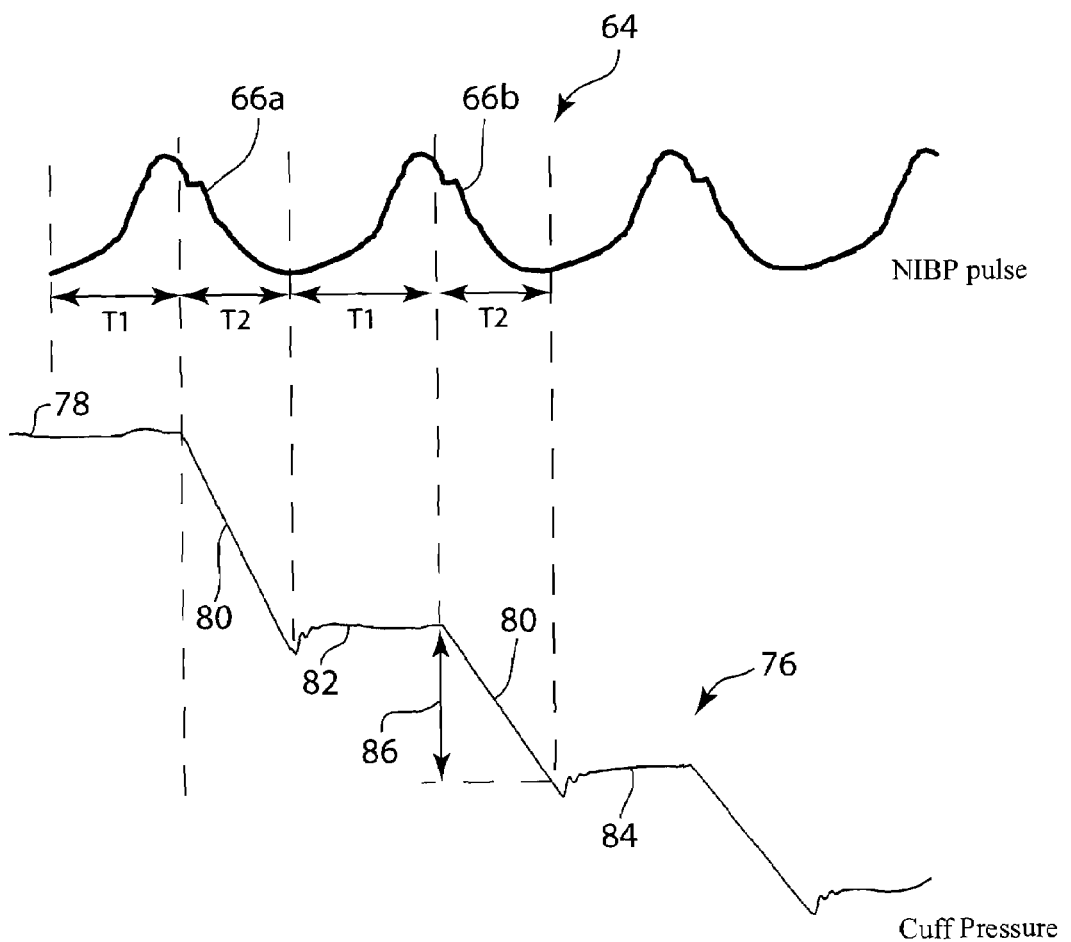
FIG. 6 is a magnified view illustrating the timing of the deflation of the blood pressure cuff during the "deflation period" of the NIBP oscillation.

Referring now to FIG. 6, thereshown is a graphic illustration of the NIBP waveform 64 and the cuff pressure 76 when the NIBP monitoring system is operated in accordance with the present invention. Initially, the cuff pressure 76 is at a first pressure level 78 during the first oscillation pulse 66a. During the timing period T1, the NIBP monitoring system determines the oscillation pulse amplitude for the oscillation pulse 66a.

Once the timing period T1 ends, the deflate valve of the NIBP monitoring system is opened, causing the cuff pressure to deflate from the first pressure level 78, as shown by the declining portion 80 of the cuff pressure graph 76. Specifically, the deflate valve is opened for a cuff deflation time T2 and the cuff pressure is allowed to decrease based upon the time the deflate valve is open. As previously indicated, the cuff deflation time T2 is calculated from the $SpO_2$ plethysmographic waveform and is selected to be slightly less than the time period from the systolic peak to the diastolic point of the next oscillation pulse 66b.

As shown in FIG. 6, the cuff pressure 76 drops to a second pressure level 82 prior to the beginning of the next oscillation pulse 66b. During the timing period T1 for the second oscillation pulse 66b, the NIBP monitoring system again calculates the oscillation pulse amplitude for the second pressure level 82. Following the termination of the timing period T1, the cuff pressure is again deflated during the deflation period T2 until the pressure reaches the third pressure level 84. This process is repeated until the NIBP monitoring system has reduced the cuff pressure below the diastolic pressure, such that the blood pressure estimate for the patient can be calculated.

In the embodiment of the invention illustrated in FIG. 6, each of the pressure steps between the respective pressure levels 78, 82 and 84 is dictated by the ability of the deflate valve to release pressure from the pressure cuff during the deflation period T2. The amount of pressure decrease, as illustrated by arrow 86, between each of the pressure levels is dictated by the physical properties of the deflate valve. In one embodiment of the invention, the deflate valve is able to decrease the pressure level between 18 and 23 mmHg in approximately 0.31 seconds. Since the deflate period T2 may be in the range of 0.3-0.6 seconds, the pressure step from each of the pressure levels could be between 18-23 mmHg. However, it should be understood that the processor of the NIBP monitoring system could also control the deflate valve to decrease the pressure levels any pressure amount desired as long as the time to decrease the pressure of the blood pressure cuff is less than the deflation period T2.

As described above, the NIBP monitoring system functions to record only a single oscillation pulse amplitude at each of the pressure levels 78, 82 and 84. Additionally, the cuff pressure level is deflated during the second half of each oscillation pulse 66 to the next pressure level such that an oscillation pulse amplitude can then be recorded for the next oscillation pulse. In this manner, the amount of time required to obtain the oscillometric envelope for the patient can be greatly reduced as compared to the typical operation of an NIBP monitoring system shown in FIG. 2.

In the embodiment of the invention described above, the cuff deflation time T2 is described as being the second half of each of the NIBP oscillation pulses following the systolic peak. However, it is contemplated that the cuff deflation time could be less than the period T2 to ensure that the pressure level has stabilized before the beginning of the next oscillation pulse. Alternatively, the deflation time could be increased to a value greater than the deflation period T2, such as (T1+ 2*T2). If the cuff deflation period is extended as described, an oscillation pulse amplitude would then be obtained from every other pulse within the NIBP waveform. If an oscillation pulse amplitude is determined every other pulse, the amount of time required to obtain a blood pressure estimate from a patient will still be decreased significantly from the prior art method illustrated in FIG. 2, which required two oscillation amplitudes to be obtained from each pressure level.

When the NIBP monitoring system 10 is operated in accordance with the method described above, a larger number of oscillation pulse amplitudes will be obtained over an increased number of pressure levels, since the pressure steps between each pressure level are contemplated as being smaller than the previously typical pressure steps between pressure levels. In this manner, a significant number of pulse amplitudes will be collected at a larger number of cuff pressures, which results in a more reliable blood pressure computation without compromising processing speed.

When the NIBP monitoring system 10 is operated in the manner described above, the concept of pulse amplitude matching at each pressure level has been eliminated since only a single pressure amplitude is obtained at each pulse 66 is validated and the stored amplitude and cuff pressure are maintained within memory of the central processor. However, if the $SpO_2$ pulse is not detected within the time differential, the NIBP pulse 66 is designated as an artifact and the amplitude information from the NIBP pulse is not used in the NIBP determination.

As an alternative to completely rejecting the NIBP amplitude when an $SpO_2$ pulse is not detected, a weighting factor may also be assigned to the determined NIBP pulse amplitude depending upon the quality of the NIBP pulse 66. As an example, the size, shape and amplitude of the NIBP pulse 66 can be compared to previously received pulses and a weighting value assigned to the amplitude measurement based upon the quality of the pulse. It is contemplated that the weighting factors may range between zero and ten, with zero being a completely rejected pulse amplitude and ten being a perfectly acceptable pulse based upon prior detection.

Figure 7:
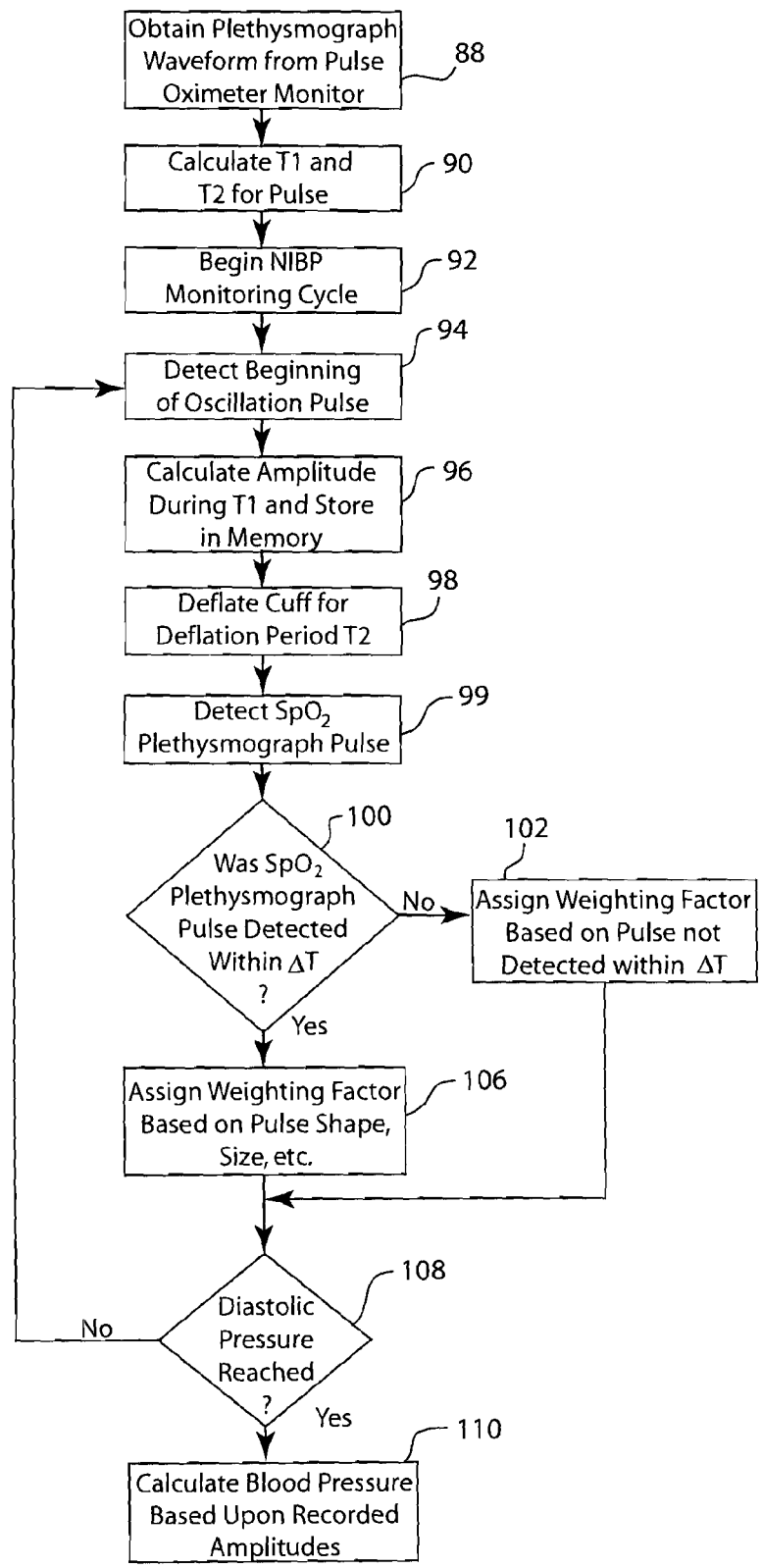
FIG. 7 is a flowchart illustrating the operational sequence utilized by the system and method of the present invention to determine the blood pressure of a patient using an NIBP monitor and a pulse oximeter sensor.

Referring now to FIG. 7, thereshown is a flowchart illustrating the operational sequence of the NIBP monitoring system in accordance with one embodiment of the present invention. As indicated in FIG. 7, the NIBP monitoring system continuously receives a plethysmographic waveform from the SpO$_2$ monitor, as illustrated in step 88. The central processor of the NIBP monitoring system calculates both a timing period T1 and a deflation period T2 based upon the SpO$_2$ pulses received as part of the plethysmographic waveform in step 90. As described, the timing period T1 and the deflation period T2 calculated from the SpO$_2$ pulses correspond to the same time periods within the oscillation pulse 66 shown in FIG. 4.

Once the timing period T1 and the deflation period T2 have been calculated, the NIBP monitoring cycle begins in step 92 and the central processor monitors for the beginning of a first oscillation pulse in step 94.

Upon receipt of the first oscillation pulse, the central processor of the NIBP monitoring system calculates an oscillation pulse amplitude during the timing period T1 and stores the oscillation pulse amplitude and the current cuff pressure level within memory, as shown in step 96. Immediately following the expiration of the NIBP pulse 66. As an example, the size, shape and amplitude of the NIBP pulse 66 can be compared to previously received pulses and a weighting value assigned to the amplitude measurement based upon the quality of the pulse. It is contemplated that the weighting factors may range between zero and ten, with zero being a completely rejected pulse amplitude and ten being a perfectly acceptable pulse based upon prior detection. If the weighting factor is larger than some predetermined threshold, the pulse will be used in the calculation of blood pressure. Therefore, even if the plethysmographic pulse delay does not support the use of the cuff pulse, other criteria may be more important and override disposal of the cuff oscillation amplitude.

Although the method of monitoring for the presence of a plethysmographic pulse within the time differential ΔT either before or after the NIBP pulse has been described in the preferred embodiment as being incorporated along with the method of deflating the pressure cuff during the deflation period of each pulse, it should be understood that these two methods could be implemented independently from each other. As an example, the pressure cuff could be deflated using conventional constant pressure step deflation techniques where a single pulse amplitude is detected at each pressure step. During the deflation of the cuff, the detection of the plethysmographic pulse 62 within the time differential ΔT determines a weighting factor for the pulse amplitude. Likewise, the concept of utilizing the weighting factor to categorize each of the pulse amplitudes could be eliminated and other methods of analyzing the pulse amplitude to determine whether the pulse amplitude should be used could be incorporated with the deflation of the pressure cuff during the deflation period of each oscillation pulse.

Referring now to FIG. 7, thereshown is a flowchart illustrating the operational sequence of the NIBP monitoring system in accordance with one embodiment of the present invention. As indicated in FIG. 7, the NIBP monitoring system continuously receives a plethysmographic waveform from the pulse oximeter monitor, as illustrated in step 88. The central processor of the NIBP monitoring system calculates both a timing period T1 and a deflation period T2 based upon the SpO$_2$ pulses received as part of the plethysmographic waveform in step 90. As described, the timing period T1 and the deflation period T2 calculated from the SpO$_2$ plethysmographic pulses correspond to the same time periods within the cuff oscillation pulses 66 shown in FIG. 4. Thus, in an alternate embodiment, the periods T1 and T2 could be calculated from the NIBP oscillation pulses 66.

Once the timing period T1 and the deflation period T2 have been calculated, the NIBP monitoring cycle begins in step 92 and the central processor monitors for the beginning of a first oscillation pulse in step 94.

Upon receipt of the first oscillation pulse, the central processor of the NIBP monitoring system calculates an oscillation pulse amplitude during the timing period T1 and stores the oscillation pulse amplitude and the current cuff pressure level within memory, as shown in step 96. Immediately following the expiration of the timing period T1, the central processor opens the deflate valve to deflate the pressure cuff for the deflation period T2, as illustrated in step 98. As previously described, the deflation period T2 is the amount of time immediately following the expiration of the timing period T1 until the diastolic point for the next oscillation pulse. Alternatively, the deflation period T2 can be slightly decreased or increased depending upon the operation of the NIBP monitoring system.

As the pressure cuff is being deflated, the central processor of the NIBP monitoring system initially detects the beginning of an SpO$_2$ plethysmographic pulse in step 99. Once the pulse is detected, the central processor monitors to determine whether an SpO$_2$ plethysmographic pulse has been detected within the time differential ΔT plus or minus a small offset, as illustrated in step 100. As described in FIG. 5, the time differential ΔT is constant and depends on the physical location of the blood pressure cuff and the finger probe. Thus, if the oscillation pulse 66 results from an actual patient heartbeat, the corresponding SpO$_2$ pulse 62 will follow within the time differential ΔT. If an SpO$_2$ plethysmographic pulse is not detected within the time differential ΔT, the processor assigns a weighting factor to the stored pulse amplitude in step 102 that is based on other criteria to determine if the cuff pulse is going to play a part in the calculation of the blood pressure for the patient. If an SpO$_2$ plethysmographic pulse is detected within the period ΔT, a weighting factor will still be assigned for the cuff pulse amplitude in step 106, but the weighting factor will be much higher than when the SpO$_2$ pulse is not detected within an appropriate time.

If an SpO$_2$ plethysmographic pulse is detected in step 100, the NIBP monitoring system determines the pulse shape, size and other parameters in step 106 and assigns a weighting factor to the pulse. The assignment of a weighting factor can be based on various parameters of the detected pulse, as is well known in the prior art.

Following the assignment of the weighting factor in either step 102 or 106, the NIBP monitoring system determines whether the diastolic pressure has been reached in step 108. If diastolic pressure has not been reached, the system returns to step 94 to detect the next oscillation pulse. However, if the diastolic pressure has been reached, the system calculates the patient's blood pressure in step 110. The calculation of the patient's blood pressure in step 110 depends upon the recorded pressure amplitudes and assigned weighting factors. The calculation of the patient blood pressure based upon the oscillation pulse amplitudes is well known, as described in the patents described previously.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A method of monitoring blood pressure in a patient, the method comprising the steps of:
    providing a non-invasive blood pressure (NIBP) monitor having a selectively inflatable and deflatable blood pressure cuff and at least one pressure transducer for detecting oscillation pulses from the patient;
    acquiring a waveform of the patient, the waveform having a series of time-spaced pulses each representing a patient heartbeat;
    analyzing the waveform to determine a timing period and a deflation period based upon the waveform;
    inflating the pressure cuff to a first pressure level;
    detecting the beginning of one of the oscillation pulses from the pressure transducer;
    determining the amplitude of the oscillation pulse at the first pressure level during the timing period following the beginning of the oscillation pulse; and
    deflating the blood pressure cuff during the deflation period to a second pressure level, wherein the deflation period follows the timing period.

2. The method of claim 1 wherein the timing period is the amount of time from a diastolic point of the patient heartbeat to the peak of the pulse.

3. The method of claim 2 wherein the deflation period is less than the amount of time from the peak of the pulse to the diastolic point of the next pulse.

4. The method of claim 1 wherein the deflation of the blood pressure cuff occurs during the deflation period independent of the pressure reduction during deflation of the pressure cuff.

5. The method of claim 1 wherein the waveform is a plethysmographic waveform received from a pulse oximeter sensor.

6. The method of claim 1 wherein the blood pressure cuff is deflated to the second pressure level during a portion of a single oscillation pulse.

7. The method of claim 1 wherein the amplitude of only a single oscillation pulse is detected at each pressure level.

8. The method of claim 1 further comprising the steps of:
    deflating the pressure cuff in a series of pressure steps each determined by the deflation period;
    determining the amplitude of a single oscillometric pulse at each pressure level; and
    determining the systolic pressure, mean arterial pressure and diastolic pressure for the patient based upon the amplitude of the oscillation pulses determined at each pressure level.

9. A method of monitoring the blood pressure of a patient, the method comprising the steps of:
    providing a non-invasive blood pressure (NIBP) monitor having a selectively inflatable and deflatable blood pressure cuff and at least one pressure transducer for detecting oscillation pulses from the patient;
    acquiring a plethysmographic waveform of the patient, the plethysmographic waveform having a series of time-spaced plethysmographic pulses each representing a patient heartbeat;
    analyzing the plethysmographic waveform to determine a timing period;
    inflating the blood pressure cuff to an initial inflation pressure;
    detecting the beginning of an oscillation pulse from the pressure transducer at a first pressure level of the blood pressure cuff;
    determining the amplitude of the oscillation pulse during the timing period immediately following the beginning of the oscillation pulse;
    deflating the blood pressure cuff for a deflation period after the timing period to a second pressure level, wherein the deflation occurs during the oscillation pulse; and
    storing the amplitude of the oscillation pulse in a processor of the NIBP monitor.

10. The method of claim 9 further comprising the steps of:
    deflating the pressure cuff in a series of pressure steps each determined by the deflation period; and
    determining the amplitude of only a single oscillation pulse at each pressure step.

11. The method of claim 10 further comprising the steps of:
    determining a time differential between the cuff oscillation pulse and the plethysmographic pulse for the same patient heartbeat;
    monitoring for the presence of the plethysmographic pulse within the time differential following the determination of the amplitude of the oscillation pulse; and
    discarding the stored amplitude when the plethysmographic pulse is absent within the time differential.

12. The method of claim 11 wherein the time differential follows the oscillation pulse when the plethysmographic waveform is obtained from a pulse oximeter sensor.

13. The method of claim 10 further comprising the steps of:
    determining a time differential between the cuff oscillation pulse and the plethysmographic pulse for the patient heartbeat;
    monitoring for the presence of the plethysmographic pulse within the time differential following the determination of the amplitude of the oscillation pulse; and
    assigning a weighting factor to the stored amplitude based upon the timing between the plethysmographic pulse and the cuff oscillation pulse.

14. The method of claim 13 further comprising the steps of:
    selectively discarding stored oscillation amplitudes based upon the weighting factor; and
    determining the systolic pressure, mean arterial pressure and diastolic pressure for the patient based upon the amplitude of the remaining oscillation pulses determined at each pressure step.

15. The method of claim 9 wherein the blood pressure cuff is deflated for the deflation period independent of the pressure reduction within the blood pressure cuff.

16. The method of claim 9 wherein the deflation period is the amount of time from the peak of the plethysmographic pulse to the diastolic point of the next plethysmographic pulse.

17. A system for determining the blood pressure of a patient, comprising:
    a non-invasive blood pressure (NIBP) monitor including a central processor and a display;
    a blood pressure cuff positionable on the patient, the blood pressure cuff being selectively inflatable and deflatable by the NIBP monitor;
    a pressure transducer associated with the blood pressure cuff and coupled to the central processor, the pressure transducer being operable to detect oscillation pulses from the patient; and
    a sensing system configured to provide a plethysmographic waveform having a series of time-spaced plethysmographic pulses each representing a patient heartbeat;
    wherein the central processor controls the deflation of the pressure cuff from an initial inflation pressure in a series of pressure steps each defined by a deflation period determined from the plethysmographic pulses of the plethysmographic waveform.

18. The system of claim 17 wherein the remote sensing system is a pulse oximeter sensor.

* * * * *